(12) United States Patent
Gorochov et al.

(10) Patent No.: US 7,211,564 B2
(45) Date of Patent: May 1, 2007

(54) METHODS AND CONSTRUCTION AND SCREENING OF LIBRARIES OF CHEMOKINE VARIANTS

(75) Inventors: Guy Gorochov, Paris (FR); Oliver Hartley, Carouge (CH); Karim Dorgham, Ivry sur Seine (FR); Patrice Debre, Paris (FR); Robin Offord, Bernex (CH)

(73) Assignees: Universite Pierre et Marie Curie (ParisVI), Paris Cedex (FR); Universite De Geneve, Geneva (CH)

( * ) Notice: Subject to any disclaimer, the term of this patent is extended or adjusted under 35 U.S.C. 154(b) by 30 days.

(21) Appl. No.: 10/791,814

(22) Filed: Mar. 4, 2004

(65) Prior Publication Data

US 2004/0258659 A1 Dec. 23, 2004

Related U.S. Application Data

(63) Continuation of application No. PCT/EP02/11045, filed on Sep. 5, 2002.

(51) Int. Cl.
*A61K 38/00* (2006.01)
*C07K 14/00* (2006.01)
*C40B 30/04* (2006.01)

(52) U.S. Cl. .................. 514/12; 530/324; 530/325; 530/350; 530/351; 514/2

(58) Field of Classification Search ................ 435/7.1, 435/6, 4, DIG. 15, DIG. 14, DIG. 35; 530/350, 530/328, 351, 324, 325; 514/12, 2
See application file for complete search history.

(56) References Cited

OTHER PUBLICATIONS

Oliver et al, Jrnl. of Human Virology, 3(5), 242, 2000 International Meeting of Institute of human Virology.*
Berger et al., Annual Review Immunol., vol. 17, pp. 657-700, (1999).
Cocchi et al., Science, vol. 270, pp. 1811-1815, (1995).
Skelton et al., Biochemistry, vol. 34, pp. 5329-5342, (1995).
Bazan et al., Nature, vol. 385, pp. 640-644, (1997).
Imai et al., J. Biol. Chem., vol. 272, pp. 15036-15042, (1997).
Moser et al., J. Biol. Chem., vol. 268, pp. 7125-7128, (1993).
Proudfoot et al., J. Biol. Chem., vol. 271, pp. 2599-2603, (1996).
Simmons et al., Science, vol. 276, pp. 276-279, (1997).
Mack et al., J. Exp. Med., vol. 187, pp. 1215-1224, (1998).
Signoret et al., J. Cell. Biol., vol. 151, pp. 1281-1294, (2000).
Yang et al., J. Virol., vol. 73, pp. 4582-4589, (1999).
Townson et al., J. Biol. Chem., vol. 275, No. 50, pp. 39254-39261, (2000).
Smith et al., Science, vol. 228, pp. 1315-1317, (1985).
Clarkson et al., Trends Biotechnol., vol. 12, pp. 173-184, (1994).
Hart et al., J. Biol. Chem., vol. 269, pp. 12468-12474, (1994).
Mosier et al., J. Virol., vol. 73, pp. 3544-3550, (1999).
Polo et al., Eur. J. Immunol., vol. 30, pp. 3190-3198, (2000).
Proost et al., J. Biol. Chem., vol. 273, pp. 7222-7227, (1998).
Pakianathan et al., Biochemistry, vol. 36, pp. 9642-9648, (1997).
Lowman et al., J. Mol. Biol., vol. 234, pp. 564-578, (1993).
Hartley, Oliver et al.; Journal of Human Virology, vol. 3, No. 5, Sep. 2000, p. 242. XP 002233593.
Brown, K.C., Current Opinion in Chemical Biology, Feb. 2000; vol. 4, No. 1, pp. 16-21, XP002233594.
Appay, Victor et al., Trends in Immunology, vol. 22, No. 2, Feb. 1, 2001; pp. 83-87; XP004323274.
Meta, Akihiro et al., Molecular Immunology, vol. 36, No. 18, Dec. 1999, pp. 1249-1254; XP002233595.
Houimel, Mehdi et al.; European Journal of Immunology, vol. 31, No. 12, Dec. 2001, pp. 3535-3545, XP002233596.
Zeng, Q.P. et al., May 31, 2000; NCBI Database Accession No. AAF73070, XP002233597.

* cited by examiner

*Primary Examiner*—T. D. Wessendorf
(74) *Attorney, Agent, or Firm*—Birch, Stewart, Kolasch & Birch, LLP

(57) ABSTRACT

The present invention provides a method for the design and/or the selection of agonist or antagonist chemokine variants combining a phage display technology and a screening on living cells expressing the receptor of the corresponding native chemokine. It also provides RANTES variants having agonist properties towards said receptor, and methods for preventing and/or curing viral diseases, as well as clues for preventing and/or curing inflammatory or malignant diseases.

3 Claims, 6 Drawing Sheets

METHODS AND CONSTRUCTION AND SCREENING OF LIBRARIES OF CHEMOKINE VARIANTS

This Nonprovisional application is a continuation application of PCT International Application No. PCT/EP02/11045 Sep. 5, 2002, which claims priority under the Patent Cooperation Treaty to patent application Ser. No. 09/945,665 filed in UNITED STATES on Sep. 5, 2001, the entire contents of which are hereby incorporated by reference.

TECHNICAL FIELD

The present invention relates to a method for obtaining chemokine variants having an improved biological property by designing and screening a phage library using a living cell system of a phage library, to the variants obtained thereof and to the use of said variants in pharmaceutical compositions and/or in pharmaceutical treatments.

BACKGROUND

Infection of target cells by HIV-1 is initially dependent on the interaction of its envelope glycoproteins with CD4 and a seven transmembrane-spanning G protein coupled receptor (GPCR). Among the several identified GPCR coreceptors, the chemokine receptors CCR5 and CXCR4 are by far the most commonly used by HIV-1. As a consequence, these receptors have been identified as important new targets for anti-HIV treatment (1). Infection by HIV strains is inhibited by the natural ligands of the coreceptors they use. Among these are MIP-1α (CCL3), MIP-1β (CCL4) and RANTES (CCL5) for CCR5 (2), CCR1 and CCR3, and SDF-1 (CXCL12) for CXCR4 (3). These ligands are chemokines, a group of small (8–12 kDa), structurally similar proteins with important roles in development and inflammation (4).

Chemokines have the ability to recruit and activate a wide variety of proinflammatory cell types, and RANTES has been shown to elicit an inflammatory response in vivo. RANTES, along with the natural ligands for the CCR5, CCR1 and CCR3 chemokine receptor, MIP-1.alpha., MIP-1.beta., were found to inhibit human immune deficiency virus type-1 ("HIV-1") infection (2), leading to the identification of CCR5 as the major co-receptor for primary isoiates of HIV-1, HIV-2 and SIV-1 (11). However, although RANTES consistently inhibits HIV-1 replication in peripheral blood mononuclear cells, it does not block infection of primary macrophage cultures, which suggests that RANTES would not influence HIV replication in non-lymphocyte cell types.

Structurally, chemokines consist of a tightly folded core from which extends a flexible region comprising approximately ten amino terminal residues. The last few C-terminal residues themselves are mobile and exposed to the solution (5). The description of a C-terminally anchored chemokine (6), as well as C-terminally conjugated chemokines (7), suggests that relatively large entities can be accommodated at the C-terminal of chemokines without compromising biological activity. According to the current model for interaction between chemokines and their receptors (8), the flexible amino terminal region is necessary for receptor activation, whereas the tigthly-folded core contains structures necessary for receptor recognition. This "two-site" model for interaction is supported by the description of chemokine variants with altered signaling activity that were obtained by modification at the amino terminus (9–11).

These above-mentioned amino-terminally modified chemokines include aminooxypentane(AOP)—RANTES, an extremely potent inhibitor of monocytotropic CCR5-dependent (R5-tropic) strains of HIV-1 (11). The strongly enhanced anti-HIV activity of AOP-RANTES is due to its ability to bring about profound and sustained downmodulation of cell surface CCR5 (12) in a process that probably involves the induction of receptor endocytosis (13). It has recently been shown that several other amino terminally modified chemokine analogues with enhanced anti-HIV activity appear to act via similar mechanisms (14, 15).

More generally, the pivotal role of chemokines in inflammatory disease is now well established (45), and the chemokine/chemokine receptor network has been validated as a target for therapeutic intervention (46). Agents that either antagonize the activity of appropriate chemokines or achieve blockade of their receptors could be used to treat inflammatory diseases. Specific examples of clinical conditions in which either RANTES or CCR5, CCR1 and/or CCR3 have been identified as key pathogenic factors (and hence where antagonists or inhibitors would be of clinical use) include asthma, organ transplant rejection, immune complex glomerulonephritis multiple sclerosis, rheumatoid arthritis, allergic rhinitis, atopic dermatitis, viral diseases and atheroma/atheroschleosis.

In addition, a link between the chemokine/chemokine receptor network and cancer has recently been established (47) indicating roles for both RANTES (48) and CCR5 (49) in the development and maintenance of tumors. Hence agents that either antagonize the activity of appropriate chemokines or achieve blockade of their receptors could be used to treat cancer.

With this in mind, the inventors reasoned that the amino terminus of RANTES would be a promising region in which to introduce diversity as part of a search for RANTES mutants with further improved activity.

Phage display is a known technology which presents a means by which diversity in a protein structure can be coupled to rapid selection of a desired phenotype. Conventional phage display involves the panning of a library of encoded and displayed ligands against a purified target which is attached to the solid phase, usually with the displayed ligands expressed as fusion proteins, N-terminal to the gene-three protein of the phage (16). This technique has been widely applied for over a decade, allowing the isolation of ligands with high affinity and specificity for many different targets (17).

Conventional phage display techniques are not easily applied for the selection of ligands of integral membrane proteins like GPCRs. As a consequence, new phage display strategies have been adopted to allow the selection of ligands that bind to targets presented on the cell surface (18). In addition, if living cells are used for the presentation of selection targets it is possible to select for phage particles internalized by receptor-mediated endocytosis (19) and thus selecting those acting via a downmodulation of the receptor. In addition, the use of living cells allows the selection of phages not internalized by receptor-mediated endocytosis but having a selective affinity for GPCRs and acting as agonists or antagonists thereof.

A novel approach for the directed evolution of chemokines, based on the use of phage display together with living cells, would therefore appear as a powerful improvement.

SUMMARY OF THE INVENTION

The current knowledge of the mechanism of action of anti-HIV chemokines is applied to the design of a phage display strategy in order to isolate chemokine variants with improved anti-viral activity and more specifically RANTES variants. The original strategy applied herein involved (I) the introduction of diversity into the flexible N-terminal region, and (II) selection for phage displayed RANTES variants that are either internalized by cells expressing CCR5 or externally specifically bound to these cells. This approach led to the isolation of a small group of selected variants. Two of such variants proteins were synthesized chemically for further evaluation. Both show an enhanced anti-HIV-1 activity compared to RANTES.

One object of the present invention is to provide a method for the design and/or the selection of chemokines variants having agonist or antagonist property towards a ligand of animal cells GPCRs comprising the following steps:
A) obtaining a phage displayed library expressing on their surface said chemokine variants mutated within the domain responsible for their effector function,
B) having a culture of animal cells expressing on their membranes the receptor of said protein G,
C) incubating the cell culture with the phage library obtained in A),
D) harvesting the cells after removal of non specifically bond and surface receptor bound phages,
E) releasing the phages internalized in step C) by lysis of cells obtained in D),
F) infecting an $E.\ coli$ culture with the released phages obtained in E) and amplifying the clones previously internalized,
G) obtaining a phage library enriched in internalizing chemokine ligands,
H) assaying the agonist or antagonist property of the chemokine variants versus the native one.

In the present invention, the terms "variant", "mutant", "derivatives" should be considered as equivalent terms as far as the function thereof includes a specific binding with the receptor of the native form of the parent chemokine.

Another object of the present invention is to provide a method for the design and/or the selection of chemokine variants having agonist or antagonist property towards a ligand of a GPCR of animal cells comprising the following steps:
A) obtaining a phage displayed library expressing on their surface said chemokine variants mutated within the domain responsible for their effector function,
B) having a culture of animal cells expressing on their membranes the GPCR,
C) Incubating the cell culture with the phage library obtained in A),
D) Eliminating the non specifically bound phages from the cells, by a process keeping the specifically bound phages on the said receptor,
E) Incubating the cells obtained in D) with an $E.\ coli$ culture and amplifying the clones being infected by the phages bound to the said receptor on animal cells,
F) Obtaining a phage library enriched in externally bound phages,
G) Assaying the agonist or antagonist property of the chemokine variants versus the native chemokine.

An example of the chemokine variants encompassed in the methods of the invention are RANTES variants, and the GPCR expressed within the animal cells membrane is CCR5. The animal cells used in the methods of the invention are preferably human cells.

In the methods of the invention, the phage library of RANTES variants is obtained using a method comprising the following steps:
  Obtaining a DNA sequence coding for human RANTES resulting from the amplification of cDNA prepared from activated PBMCs (Peripheral Blood Monocytes Cells),
  Performing a PCR mutagenesis of the 5' portion of the DNA sequence of RANTES using a specific downstream primer and a degenerated upstream primer containing recognition sites for restriction enzymes in order to insert the PCR amplification products into the phage display vector,
  Production of the phage library by introducing the said vector containing the purified PCR products into an $E.\ coli$ culture.

The skilled person can use all the available amplification methods and/or vectors as equivalent methods for obtaining the phage display libraries. In one embodiment, the phage vector can be a phagemid like $pHEN_1(26)$.

The functional properties of the selected chemokine variants are then assayed by all the methods, including in vitro, ex vivo and in vivo methods available to the skilled person. With regards to the function of anti-virus infection, these methods include the measure of the inhibition of replication of HIV virus in isolated pBMCs, the measure of the effect of these variants on the inhibition of fusion between cells bearing the cell receptor(s) for a virus and cells bearing on their surface an envelope protein of the same virus, and/or the measure of blood monocyte-derived macrophages by a virus, and/or competition binding studies between the selected variant and the native chemokine.

With regards to calcium signaling the cytosolic calcium concentration can be measured.

Once the recombinant phages having the expected functional properties obtained, these properties could be improved by constructing a second, and if necessary a third generation of a phage displayed library by a method comprising a step of selection of variants and a step of recombination between the selected variants. These two steps can be repeated as often as necessary.

The selected variants can also been improved by all methods of DNA shuffling available in the Art.

The invention also provide RANTES variants obtainable by the methods of the invention and having the general formula AA1SPAA2SSQAA3, AA3, AA3 (SEQ ID NO: 40), in which:
  *AA1 L or an aromatic residue,
  #AA2 is L, M or V,
  AA3is S, P, T or A.

Herein, RANTES (10–68) means amino-acids 10 to 68 of the RANTES (an acronym for Regulation upon Activation, Normal T-Expressed and presumably Secreted) chemokine as listed below.

SPYSSDTTPCCFAYIARPLPRAHIKET-FYTSGKCSNPAVVFVTRKNRQVCANPEK KWVREY-INSLEMS (SEQ ID NO:40).

RANTES variants of the above general formula might have D antagonist properties towards the chemokine receptor CCR1 and/or CCR3 and/or CCR5.

The RANTES variants of the invention might also have antagonist properties towards RANTES, MIP-1α and MIP-1β.

In a preferred embodiment, the RANTES variants have a N-terminal amino-acid sequence selected among the following sequences:

LSPVSSQSSA($P_1$)(SEQ ID NO: 1), FSPLSSQSSA($P_2$) (SEQ ID NO: 2), LSPMSSQSPA(SEQ ID NO: 3), WSPLSSQSPA(SEQ ID NO: 4), WSPLSSQSSP(SEQ ID NO: 5), LSPQSSLSSS(SEQ ID NO: 6), ASSGSSQSTS (SEQ ID NO: 7), ISAGSSQSTS(SEQ ID NO: 8), RSPMSSQSSP(SEQ ID NO: 9), YSPSSSLAPA(SEQ ID NO: 10), MSPLSSQASA(SEQ ID NO: 11), ASPMSSQSSS (SEQ ID NO: 12), QSPLSSQAST(SEQ ID NO: 13), QSPLSSTASS(SEQ ID NO: 14), LSPLSSQSAA(SEQ ID NO: 15), GSSSSSQTPA(SEQ ID NO: 16), YSPLSSQSSP (SEQ ID NO: 17), FSSVSSQSSS(SEQ ID NO: 18), or, among the following sequences:

VSTLSSPAST(SEQ ID NO: 30), ASSFSSRAPP(SEQ ID NO: 31), QSSASSSSSA(SEQ ID NO: 32), QSPGSSWSAA (SEQ ID NO: 33), QSPPSSWSSS(SEQ ID NO: 34), QSPLSSFTSS(SEQ ID NO: 35), ASPQSSLPAA(SEQ ID NO: 36), LSPVSSQSSA(SEQ ID NO: 1), LSPQSSLSSS (SEQ ID NO: 6).

Wherein $P_1$ and $P_2$ were assayed for their agonistlantagonist properties of CCR5 receptor.

Both RANTES $P_1$ and $P_2$ variants have greatly enhanced anti-HIV activity relative to the wild-type protein. A number of chemokine analogues with enhanced anti-HIV activity feature hydrophobic N-terminal extensions (11, 14, 33, 34). In the construction of the library of RANTES mutants, the inventors opted to include an extra N-terminal residue, which would correspond to the methionine in Met-RANTES and Met-SDF-1 (10, 14), leucine in L-RANTES (34), and to the pentane chain of AOP-RANTES (11). Biopanning of the library led to selection of clones incorporating hydrophobic amino acids at this position. Predominant among these was leucine, although it is interesting to note that aromatic residues were also strongly favoured.

The remarkable conservation of proline at position two of chemokines has been documented (35). In the case of RANTES, there are conflicting reports as to the requirement of proline 2 for activity, both as a CCR5 agonist and as an HIV inhibitor. On the one hand, removing the first two residues of RANTES with dipeptidyl peptidase was reported to enhance its anti-viral activity (36). On the other hand, alanine scanning mutagenesis of RANTES indicated that this residue is crucial for binding to CCR5 (37). Since the vast majority of clones selected by biopanning on CCR5-expressing cells incorporate proline at position two, the experimental results obtained in the hereinafter examples suggest that this residue plays an important role in the interaction between RANTES and CCR5.

The same alanine scanning mutagenesis study (37) also revealed that tyrosine 3 makes an important contribution towards functional interaction between RANTES and CCR5. Surprisingly, both tyrosine and alanine are absent at position 3 among the clones isolated by biopanning on CCR5-expressing cells by the methods of the present invention. Instead, there is a strong selection for the hydrophobic residues leucine, methionine and valine.

The method of the inventors leads also to the selection of variants having almost exclusively glutamine at position six after biopanning on CCR5-expressing cells. The corresponding wild-type residue, aspartate, has been shown to be important for signal transduction via CCR5 (37). The postulated salt bridge between this aspartate residue and lysine 45 on the partner chain of the RANTES dimer (5) may be of significance, since it would not be formed with either glutamine at position six, and this would not be formed with either glutamine at position six, and this would presumably destabilize the dimer. If dimer destabilization was driving selection at position six, however, one would imagine equivalent selection pressure for any non-acidic residue. Therefore, glutamine 6 may well play an important role in the interaction between RANTES derivatives and CCR5.

In a more preferred embodiment, they have the formula FSPLSSQSSA (SEQ ID NO: 2)-RANTES (10–68) (P2), or LSPVSSQSSA (SEQ ID NO: 1)-RANTES (10–68) (P1).

In another preferred embodiment, clones selected by binding to CHO-CCR5, without internalization, have their N-terminal amino-acid sequence selected among the following sequences:

VSTLSSPAST(SEQ ID NO: 30), ASSFSSRAPP(SEQ ID NO: 31), QSSASSSSSA(SEQ ID NO: 32), QSPGSSWSAA (SEQ ID NO: 33), QSPPSSWSSS (SEQ ID NO: 34), QSPLSSFTSS(SEQ ID NO: 35), LSPQSSLSSS(SEQ ID NO: 6), ASPQSSLPAA(SEQ ID NO: 36), LSPVSSQSSA (SEQ ID NO: 1).

It should be noted that other variants derived from the above variants by the above methods such as DNA shuffling (41) or selection from a second or third generation phage display library are also encompassed by the present invention.

Hence, it has been shown by the inventors that the activity of one of the mutants, $P_2$, compares favourably with that of the prototypic potent anti-HIV chemokine, AOP-RANTES. $P_2$ therefore represents a promising lead compound from which further optimized inhibitors might be developed. To this end, a construction of second generation libraries has been undertaken. For example, the residues found at positions 0, 2 and 6 of the selected consensus sequence has been fixed for introducing diversity into flanking positions. This kind of approach is analogous to the "affinity maturation" strategies used to improve the activity of ligands isolated by phage display (38).

A complementary strategy would be to use total chemical synthesis to systematically dissect the active N-terminal region (residues 0 to 9) of $P_2$. Total chemical synthesis renders possible the incorporation of non-natural, non-coded structures into a protein, and thus exploration of sequence space beyond the boundaries imposed by the 20 natural amino acids. This approach has been already applied successfully to the improvement of AOP-RANTES (33).

Besides that, it is well known in the art that certain amino acids can be replaced with others without any substantial changes in the property of such polypeptides. Such replacements are designated as conservative substitutions, and are in the scope of the chemokine variants of the invention.

It should also be noted that deletions or insertions of amino acids can often be made which do not substantially change the properties of a polypeptide or even lead to improvements of these properties. The present invention includes such deletions or insertions (which may be, for example up to 10, 20 or 50% of the length of the specific antagonists sequence given above).

The present invention also includes within its scope fusion proteins in which the polypeptides of the present invention are fused to another moiety. This may be done, for example, for the purpose of labeling or for a medicinal purpose. In this case said moiety could be advantageously a polypeptide having a complementary pharmacological property leading to an improved pharmaceutical effect. Such as an example, a hybrid mutant might include a peptide moiety which binds CCR5 and a peptide moiety which binds CXCR4 receptor, for the reasons explained hereafter within the discussion section.

The polypeptides of the present invention can be produced by expression from prokaryotic or eukaryotic host cells, utilizing an appropriate DNA coding sequence. Appropriate techniques are disclosed in Sambrook et al., (2001) Molecular Cloning: A Laboratory Manual, Cold Spring Harbor, Laboratory Press, USA. Alternatively, they may be produced by covalently modifying RANTES or by total chemical synthesis.

In addition to the polypeptides discussed above, the present invention also covers DNA sequences coding such polypeptides (which may be in isolated or recombinant form), vectors incorporating such sequences and host cells incorporating such vectors which are capable of expressing the variants of the present invention.

The invention also provides pharmaceutical compositions comprising a selected RANTES variant or a pharmaceutical salt thereof, in a mixture with one or more pharmaceutically acceptable excipient.

The pharmaceutical compositions of the invention also encompass compositions comprising the DNA sequences coding such RANTES variants or vector incorporating said DNA sequences for use in gene therapy methods or the formulations of DNA vaccines.

Another aspect of the invention is a method for inhibiting or preventing HIV infection in humans comprising a step of treatment with an above captioned composition containing either a RANTES variant or a DNA sequence coding thereof of the invention.

The method might comprise the administration of the said pharmaceutical composition to humans alone or in combination with other treatments for the prevention and/or the therapy of AIDS.

Another aspect of the invention is a method for preventing and/or curing inflammatory or malignant diseases in humans comprising a step of treatment with a composition of a RANTES variant such a described above.

Another aspect of the invention is a method for treating tumors and cancer wherein RANTES and CCR5 contribute to their development. This method comprises the administration of the said pharmaceutical composition as an antagonist of RANTES and/or CCR5 as a treatment to such forms of cancer or tumors.

Discussion

Two mechanisms have been put forward to explain how potent RANTES variants inhibit HIV entry: (i), steric blockade of the interaction between HIV envelope and cell surface coreceptors (11), and (ii), reduction of cell surface coreceptor concentration via the induction of receptor downmodulation (12, 29). We investigated which of these mechanisms is responsible for the increased anti-viral activity of mutants $P_1$ and $P_2$ by measuring receptor affinity and steady-state surface receptor concentration after exposure to ligand. The hereinafter example suggests that both mechanisms contribute to he enhanced activity of mutant $P_2$. On the other hand, the improvement of mutant $P_1$ over the wild-type protein would seem to be solely due to an increase in affinity for CCR5. One could postulate that the $P_1$-phage clone was selected purely on the basis of its increased receptor affinity: while the expressed ligand does not induce a significant level of CCR5 endocytosis, its high affinity ensures that the phages particle remains cell-associated even in the stringent acid wash conditions (10 min at pH 3).

The capacity of a GPCR ligand to induce downmodulation of its cognate receptor is generally believed to be linked to agonist activity (39). We find that mutant $P_2$, which exhibits an increased capacity to induce receptor downmodulation compared to RANTES, also elicits a stronger signal via CCR5. Variant $P_1$, whose capacity to induce receptor downmodulation is indistinguishable from that of RANTES under the experimental conditions we used, is an agonist of comparable strength on HEK-CCR5 cells. Interestingly, our observation that variant $P_1$ has reproducibly lower signaling activity than RANTES on CHO-CCR5 cells suggests that cell background may play a role in the ability of a chemokine analogue to signal via its cognate receptor, and at the same time offers some hope of developing an entry inhibitor with little or no agonist activity.

A theoretical obstacle to the use of CCR5 inhibitors is the rapid rate of evolution of HIV-1 that might lead, under treatment, to the in vivo selection of viral strains using co-receptors other than CCR5 (40). Should this prove to be the case, biopanning might be used to help provide a solution. The method that was successfully applied to RANTES and CCR5 could be applied to the selection of inhibitors endowed with different receptor specificities. For instance, it might be possible to confer anti-CXCR4 activity on RANTES while retaining its original anti-CCR5 activity. To reach such a goal one might envisage using a RANTES-based library selected alternately on cells expressing CCR5 and CXCR4. Another possibility might rely on the construction of libraries of hybrid mutants through a DNA shuffling approach (41). Taking advantage of the important degree of homology in this gene family, a mixed pool of several sequences could be used for library construction.

The elaboration of chemokine variants is a strategy that is already used by viruses themselves in order to subvert or exploit the immune system (42). Our results indicate the potential of a corresponding counter-strategy: the directed evolution of chemokines into specific antivirals. Such chemokine variants could be produced with relatively low cost and ease using readily accessible recombinant techniques. In addition, they would be amenable for gene delivery approaches in vivo either as part of the formulation of DNA vaccines (43) or as stably expressed transgenes (44).

Finally, the potential applications of this approach for the selection of new GPCR ligands extends well beyond the field of AIDS. Indeed, GPCRs represent the largest group of validated drug targets in biomedical research, and since work carried out so far indicates a considerable degree of conservation of the cellular machinery required for downmodulation across this family of receptors (39), it is tempting to imagine that the "biopanning" technique could be used to isolate other, different, clinically important inhibitors or antagonists.

The drawing and examples hereafter illustrate different aspects of the invention without any limitation.

1a: cloning strategy.

Gene III with is covalently linked to RANTES DNA mutants allowing the expression of RANTES variants on the surface of the phage 1b: Directed Evolution of RANTES towards an improved anti-HIV activity.

1c: Phage-chemokine and cell-based selection.

Figure 1A:
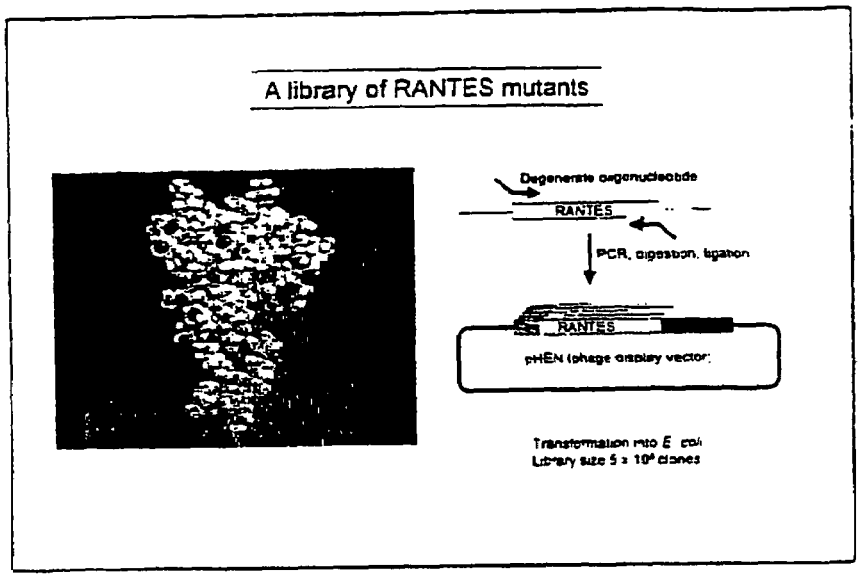
FIG. 1: strategy of the method of the invention
Figure 1B:
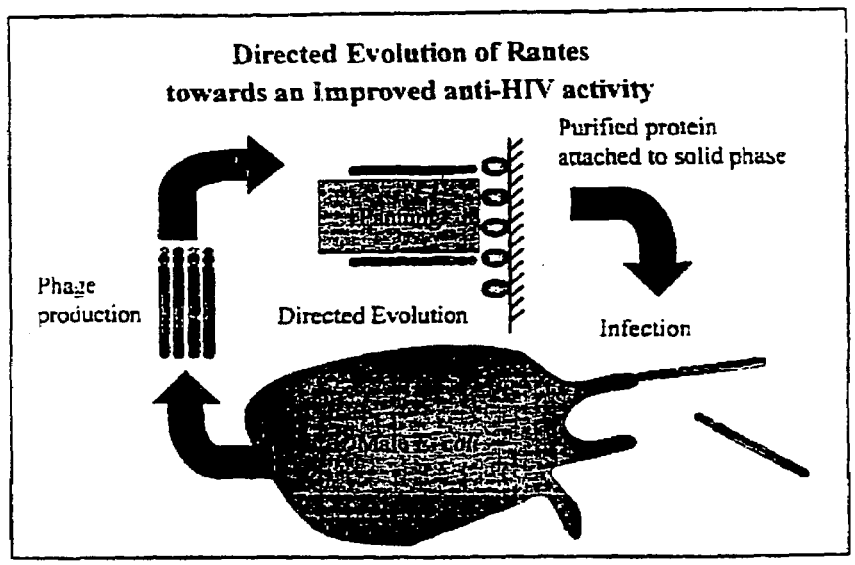
Figure 1C:
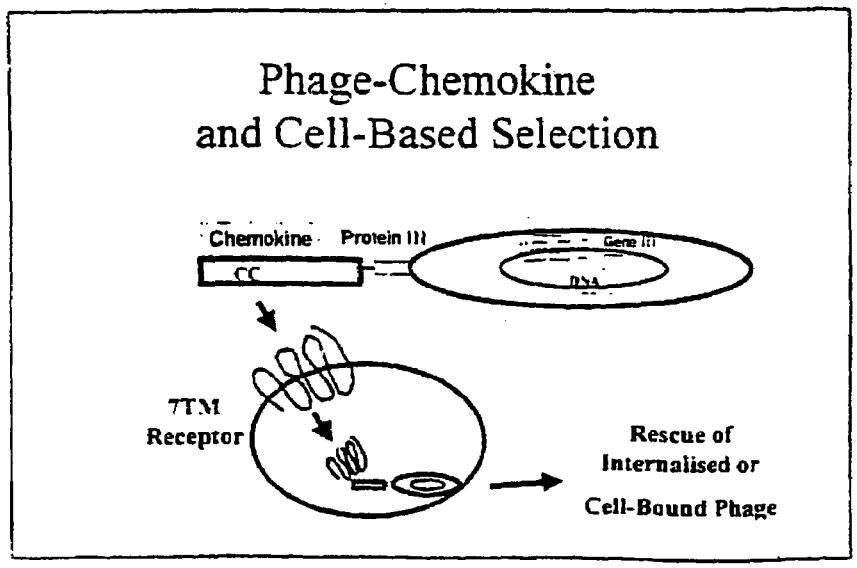
Figure 2:
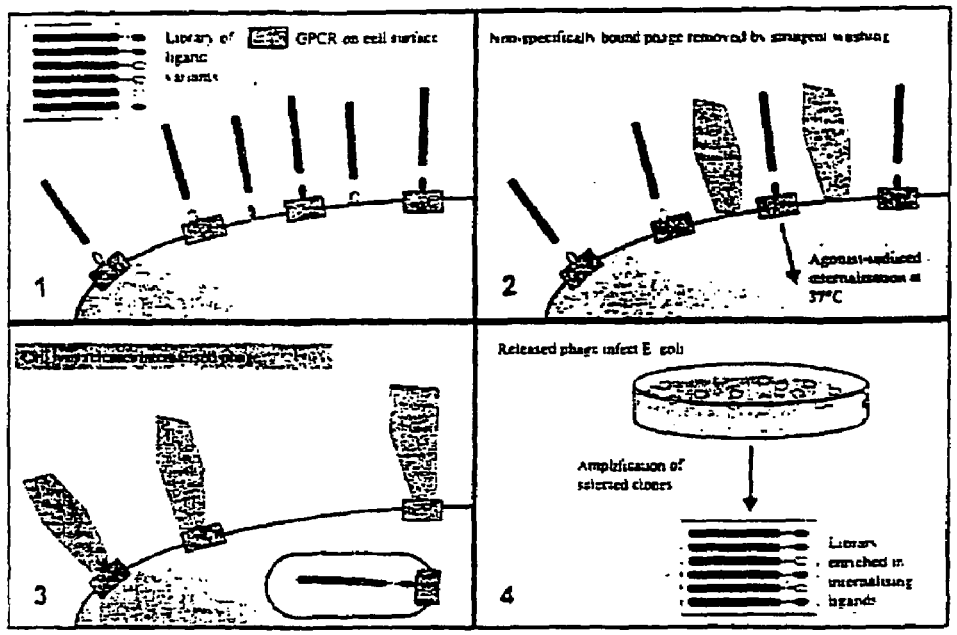

FIG. 2: Biopanning strategy.

Figure 3:
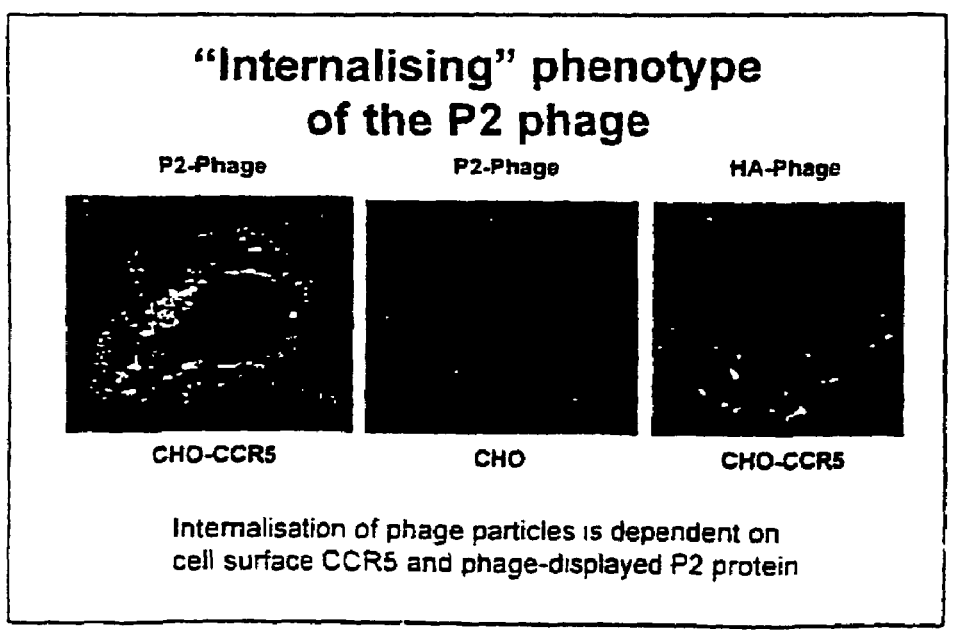

FIG. 3: Intracellular Localization of Internalized Phages. Entry into cells is dependent on cellular expression of CCR5 and phage expression of the RANTES mutant $P_2$. After incubation with either $P_2$-phage or control phage (as indicated above) CHO-CCR5 and CHO cells (as indicated below), were washed extensively, fixed, permeabilized and stained using an anti-phage coat protein antibody before analysis by confocal microscopy. The edges of each cell are indicated by dashed lines.

Figure 4:
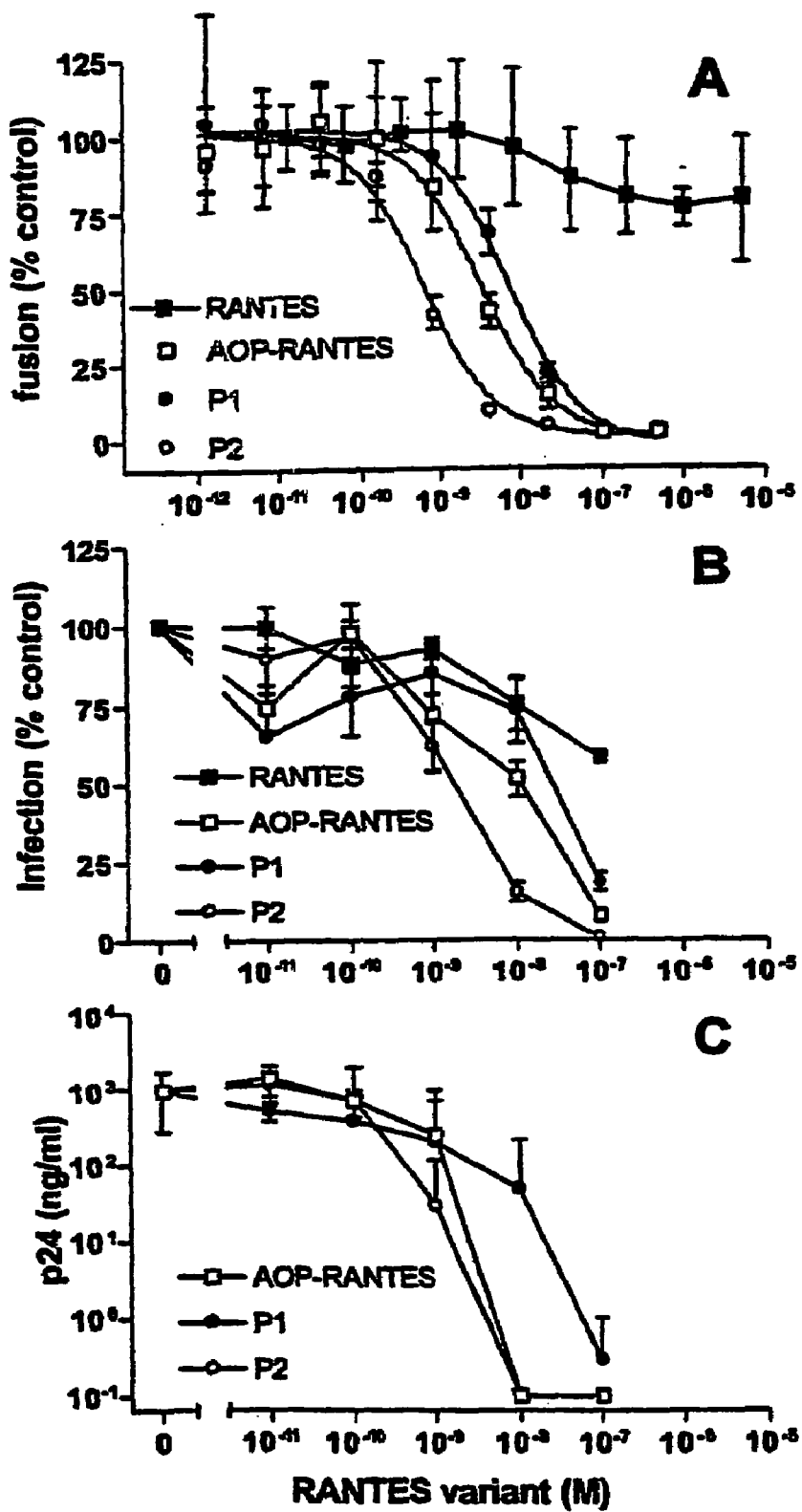

FIG. 4: Anti-HIV activity of RANTES variants. A. R5-tropic envelope-dependent cell fusion assay. $P_1$ and $P_2$ prevent R5-envelope-mediated cell fusion more efficiently than RANTES. Error bars indicate minima and maxima. $P_2$ is more effective than AOP-RANTES ($IC_{50}$ values of 0.6 nM (0.4–0.9) and 3 nM (2–6), respectivly; 95% confidence intervals in brackets. B. Infection of macrophages by HIV-1 particles pseudotyped with the BaL envelope. Whereas RANTES does not achieve 50% inhibition in the concentration range used, $P_1$ and $P_2$ achieve 50% inhibition between $10^{-8}$–$10^{-7}$ M and $10^{-9}$–$10^{-8}$ M, respectively. The corresponding value for AOP-RANTES is approximately $10^{-8}$ M. Error bars indicate s.e.m. C. Replication of the field isolate, BXO8, in activated PBMCs. While $P_1$ is active at concentrations above $10^{-8}$ M, both AOP-RANTES and $P_2$ strongly inhibit replication at concentrations above $10^{-9}$ M. Error bars indicate 95% confidence interval.

Figure 5:
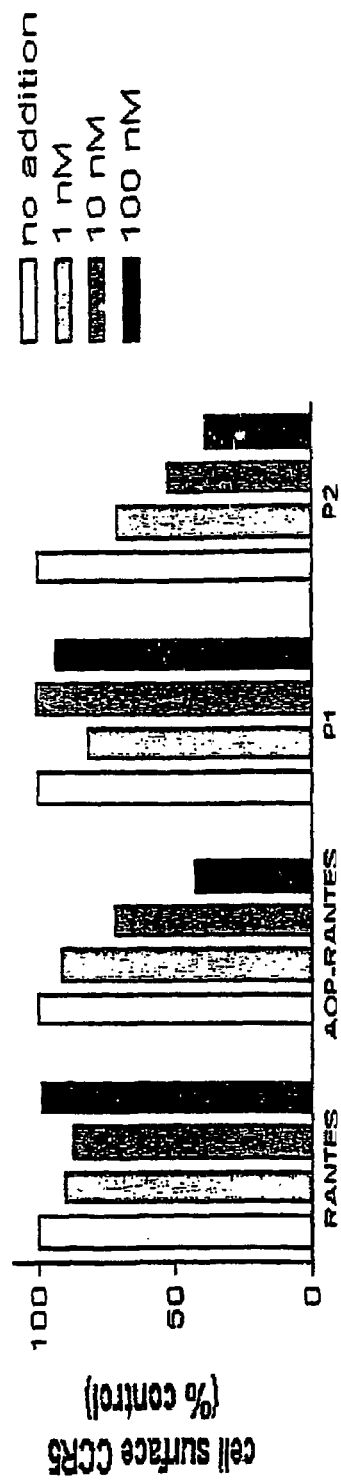
Figure 5:
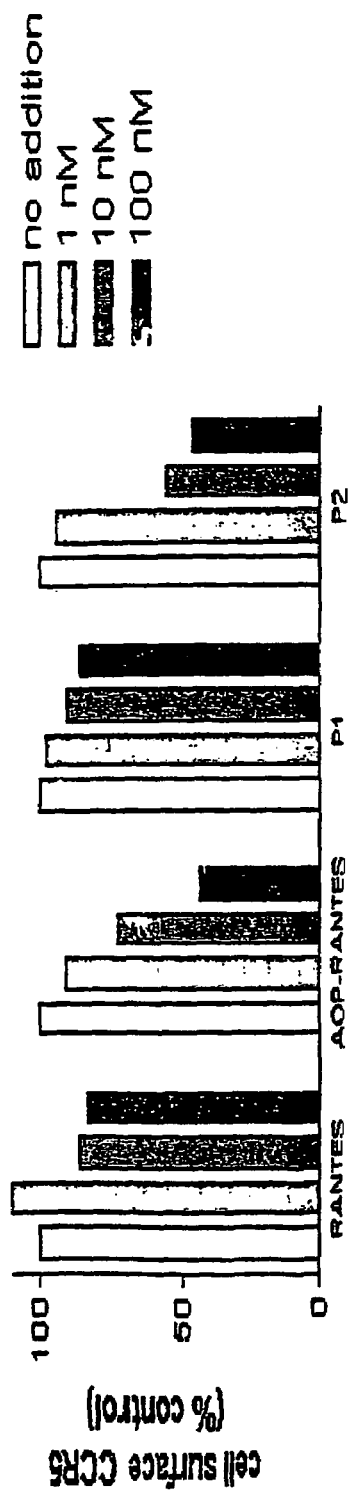

FIG. 5: CCR5 internalization induced by RANTES and RANTES variants. $P_2$ and AOP-RANTES induce dose-dependent receptor downmodulation. Steady-state levels of surface CCR5 were measured by flow cytometry after incubation with chemokines. Levels are expressed as percentage of control (medium, no chemokine). These data are representative of three independent experiments performed under identical conditions.

Figure 6:
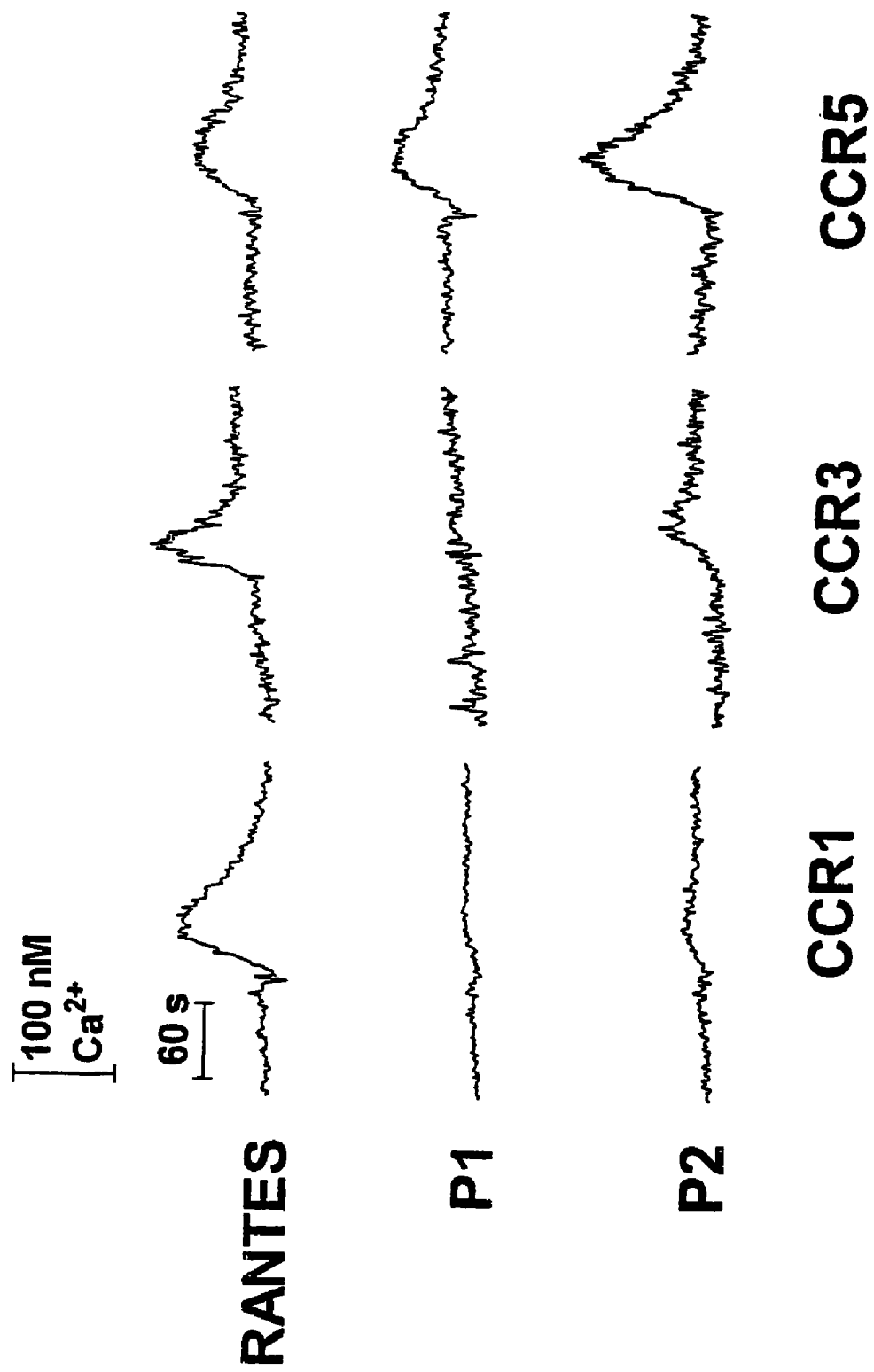

FIG. 6: Signaling activity of RANTES variants via RANTES receptors. The signaling activities of RANTES (top), P1 (middle) and P2 (bottom) via CCR1, CCR3 and CCR5 (as indicated) were measured in stably transfected HEK cells that had been loaded with Fura-2. Cytosolic calcium-dependent fluorescence changes in response to chemokines (100 nM) were measured. The traces are representative of at least three independent experiments performed under identical conditions.

Figure 7:
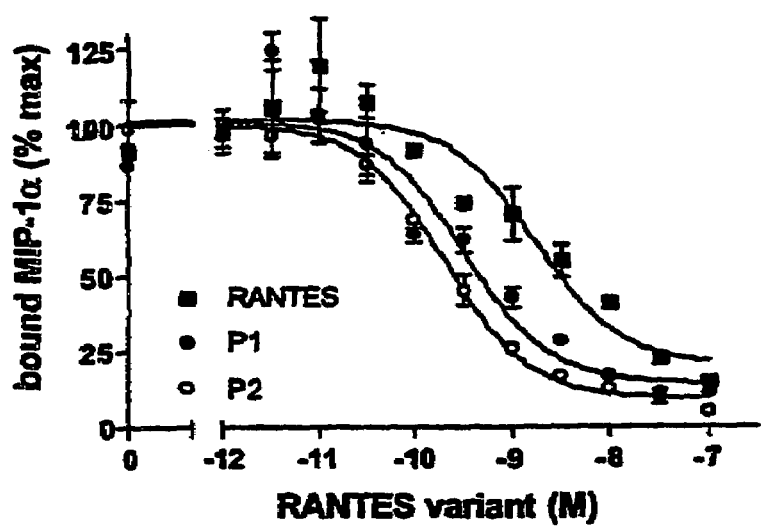

FIG. 7: Affinity of RANTES variants for CCR5. Competition binding assay on CHO-CCR5 cells using [$^{125}$I] MIP-1α as tracer. The selected mutants $P_1$ and $P_2$ have significantly higher affinity than RANTES ($IC_{50}$ values of 0.3 nM, 0.2 nM and 1.7 nM respectively).

Figure 8:
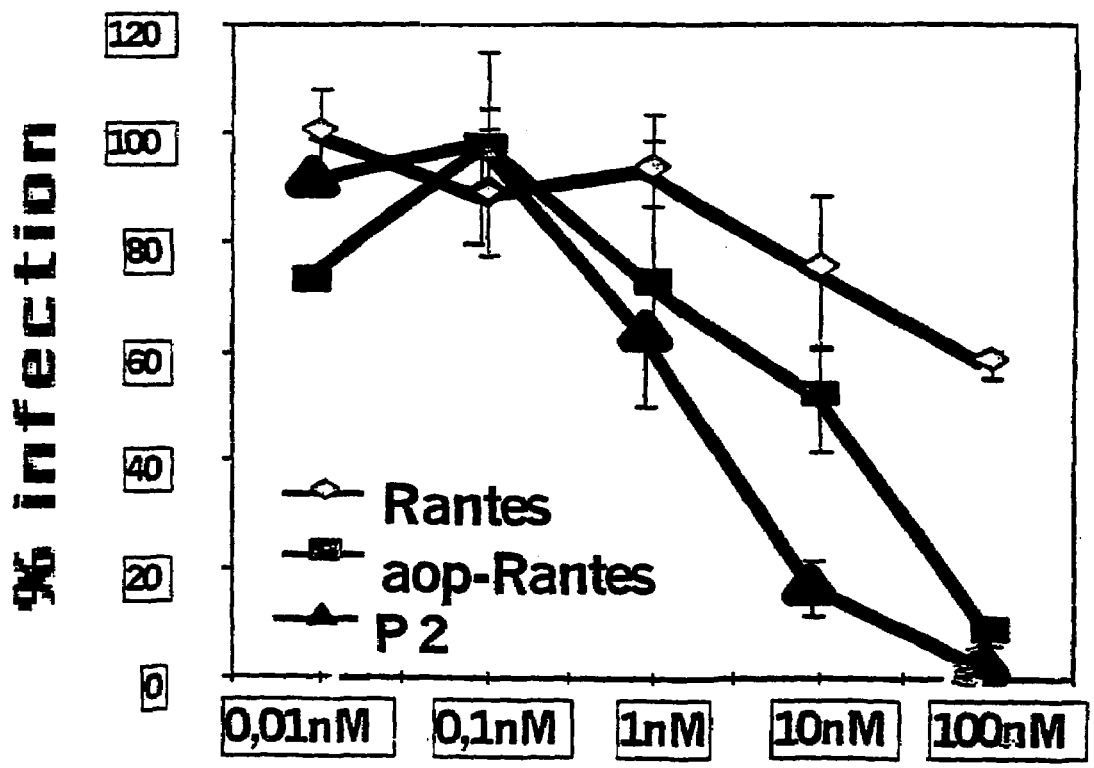

FIG. 8: Infection of Blood Monocytes-derived Macrophages by Primary HIV-1 Strain BaL (R5) in the presence of Wild Type or Modified RANTES.

METHODS

Reagents

RANTES and the mutants $P_1$ and $P_2$ were prepared by total chemical synthesis. Briefly, peptides corresponding to RANTES (1–33) and RANTES (34–68) were produced by solid phase peptide synthesis using a modified Applied Biosystems 430A peptide synthesizer and the protocols of Hackeng et al (20). To produce full-length chemokines, the Native Chemical Ligation approach was used (21). Formation of disulphide bridges was performed as described in (22). The AOP-RANTES used in this study was from the batch described in reference (11). The 1D2 anti-RANTES antibody was obtained from Pharmingen (San Diego, Calif., USA). The anti-M13 antibody was obtained from Amersham Pharmacia Biotech was FITC-labelled in the laboratory according to standard procedures.

Cells

CHO-K1 parental cells were provided by BioWhittaker. CHO—CCR5 were kindly provided by T. Schwartz (Panum Institute, Copenhagen). HEK-CCR5 (23) and HEK-CX3CR1 cells (24) were a kind gift from C. Combadiere (Hôpital Pitié-Salpétrière, Paris). HEK293T and CHO-K1 cells were cultured in RPMI 1640 supplemented with 10% heat-inactivated FCS (Life Technologies), 0.3 mg/ml L-glutamine, 100 U/ml penicillin and 100 μg/ml streptomycin (penicillin/streptomycin). Transfected cells were maintained in medium containing 1 mg/ml G418 (Life Technologies). Both cell lines used for the cell fusion assay, HeLa-P5L (11) and HeLa-Env-ADA (25), were kindly provided by M. Alizon (Institut Cochin, Paris). HeLa-P5L were maintained in DMEM supplemented with 10% heat inactivated FCS, penicillin/streptomycin and 500 pg/ml Zeocin (invitrogen). Hela-Env-ADA cells were maintained in the same medium containing 5 μM methotrexate instead of Zeocin.

Human peripheral blood mononuclear cells (PBMCs), isolated on Ficoll gradients (Phamacia Biotech) from the buffy coats of healthy donors seronegative for HIV, were cultured for 72 h in RPMI 1640 medium supplemented as described above. PBMC were stimulated with 1 μg/ml phytohaemaglutinin (Murex Diagnostics, U.K.), for 72 hours. The cells were then cultured in the presence of 500 U/ml IL-2 (Chiron) for 24 hours prior to viral challenge. Monocyte-derived macrophages (MDM) were derived from freshly isolated PBMC. After one hour culture in supplemented RPMI 1640, adherent cells were culture overnightin medium supplemented with 10% human AB serum (ABS). Adherent cells were then detached by incubating at 4° C. and by gentle scraping with a rubber policeman. Monocytes were cultured for 7 days in Teflon bags in medium supplemented with 15% ABS. MDM were then harvested and washed extensively. At the end of the procedure, cells were >98% macrophages as assessed by morphology and by flow cytometry (CD14+, CD16+).

Library construction

The DNA sequence encoding tag HA 1.1 (YPYDVPDYA) (SEQ ID NO: 19) was cloned into the phagemid pHEN1 (26), kindly provided by G. Winter, between restriction sites NcoI and NotI. The DNA sequence coding for human RANTES, amplified from cDNA prepared from activated human PBMCs, was used as the scaffold for library construction. PCR mutagenesis of the 5' portion of the gene was performed using a specific downstream primer 5'-TGG GGCCCCTCTAGA CAT CTC CAA AGA GTT GAT GTA CTC (SEQ ID NO: 20) (the recognition sites for PspOMI and XbaI—in that order—are underlined) and a degenerate uptream primer 5'-CTC GCG GCC CAG CCG G CCATGGCC NNK TCC NCA NNK TCC TCG NNK NCC NCA NCC TGC TGC TTT GCC TAC ATT GC GCGGCCGCTG CCC CGT GCC CAC ATC (SEQ ID NO: 21) (underlined: recognition sites for NcoI and NotI). The purified PCR product was cut with NcoI and PspOMI and inserted into pHEN1, previously linearized using NcoI and NotI. The ligated DNA was electroporated into *Escherichia coli* TG1. Cells were grown for 1 hour in SOC medium at 37° C., and then plated on LB-agar dishes containing 100 μg/ml ampicillin and 1% (w/v) glucose. Certain colonies were screened by PCR before selection and their DNA insert was sequenced using an automatic sequencer ABI 377 (Perkin Elmer, USA). In this way the complexity of the expressed library was determined to be at least $5\times10^6$, thus exceeding its theoretical diversity ($2\times10^6$: the number of possible combinations of amino acids). Phage stocks were prepared essentially as in (26).

Biopanning

Phage stocks used for selection or staining were supplemented with 1.5% (w/v) BSA prior to their use. $10^{10}$ cfu of phage were directly incubated with $5×10^6$ adherent cells growing in 6-well plates (Nunc, Denmark) at 37° C., 10% $CO_2$, in 5 ml of supplemented RPMI 1640 medium. After 1 hour, cells were washed 10 times at room temperature with 10 ml of PBS and then scraped from the plate into 10 ml of PBS 1% (w/v) BSA. Cells were pelleted at (1600 rpm; 10 min; 4° C.), then resuspended in 1 ml of elution buffer (0.1M glycine-HCl, pH 3) and kept on ice for 10 min. The cell suspension was then neutralized with 1 M ris-Cl (pH8) and pelleted Cells were then resuspended in Tris (30 mM, pH 8), EDTA (1 mM) and were lysed by 3 cycles of freezing (-80° C.) and thawing (37° C.). The total cell lysate was pre-warmed to 37° C. and mixed with log-phase E. coli TG1. After 1 hour incubation at 37° C. the mixture was plated on LB-agar containing 100 µg/ml ampicillin and incubated overnight at 37° C. After picking isolated colonies for sequencing with primers LMB3 and pHEN-SEQ (42), the remainder were scraped from the plates for the production and purification of phages (as described above) for use in further rounds of biopanning.

Fluorescence Detection of Phage Associated with Target Cells

CHO cells ($10^3$–$10^4$) were seeded onto glass slides. 12 hours later, cells were incubated with monoclonal preparations of phage ($10^{11}$ t.u./ml), which had previously been blocked with 1.5% (w/v) BSA at 37° C. for 1 hour. Cells were then washed 10 times at room temperature with PBS and incubated 10 min in ice-cold 0.1 M glycine-HCl (pH 2.8). After neutralization with 1 M Tris-HCl (pH 8), cells were washed again once with PBS, fixed for 10 min at room temperature in 4% paraformaldehyde, and permeablized using 0.1% Triton X100 (Sigma) in PBS-BSA (15 min on ice). After a further wash with cold PBS-BSA, the slides were incubated for 1 hour on ice with 2.5 µg/ml FITC-labeled anti-M13 antibody in PBS-BSA. After 2 final washes with cold PBS-BSA, slides were air-dried before mounting with EUKITT medium (Kindler, Germany) and examined on a Leica scanning confocal microscope.

Competitive Radioligand Binding to CCR5

Assays were carried out essentially as (11). CHO-CCR5 cells were seeded into 24 well plates ($8×10^4$ cells/well). After overnight incubation, competitive binding was performed on whole cells at 4° C. using 12 pM [$^{125}$I]MIP-1-α (Amersham) plus variable amounts of unlabelled ligand. After incubation, cells were washed, lysed, and the lysaes counted using a Beckman Gamma 4000 scintillation counter. Determinations were performed in duplicate and $IC_{50}$ values derived from monophasic curves (competition binding; one-site) fitted using Prism software (GraphPad).

Calcium Mobilisation Assay

Experiments were carried out essentially as described in (27). Fluorescence measurements were carried out on cells loaded with Fura-2 using an LS-50 spectrofluorimeter (Perkin-Elmer, Cetus) maintained at 37° C. Cytosolic $Ca^{2+}$ concentrations were calculated from the Fura-2-fluorescence according to the formula of Grynkiewicz et al. (28).

Cell-Fusion Assay

CCR5-tropic viral envelope-mediated cell fusion assays were carried out as described in reference (29). Experiments were performed in triplicate and dose-inhibition curves were fitted to the data using Prism software (GraphPad).

Viral challenge

The primary R5 strain HIV-$1_{BX08}$ and the laboratory adapted HIV-$1_{BaL}$ were obtained from the supernatants of infected PHA-activated PBMC harvested at the peak times of Gag p24 production. Activated PBMC ($10^5$) in triplicate wells were treated for 30 min at 37° C. with medium alone or medium containing serial dilutions of chemokines. HIV-1 BX08 (m.o.i. $2×10^{-5}$) or HIV-$1_{BaL}$ at a m.o.i. of $10^{-4}$ (not shown) was then added. After overnight incubation, cells were washed extensively and cultures in medium containing appropriate concentrations of chemokines. Quantitative HIV-1 p24 antigen capture ELISA was performed on the supernatants according to the manufacturer's instructions (Beckman Coulter, France). Cell viability was not affected by the chemokines used in this assay.

Single-Round Infectivity Assay

The pNL-Luc-E$^-$R$^+$ vector is a derivative of the HIV-$1_{NL4-3}$ provirus defective in envelope gene and bearing the luc gene encoding luciferase in place of the nef gene (30). The HIV-$1_{BaL}$ envelope expression vector is the pSV7d plasmid bearing the R5 HIV-$1_{BaL}$ env gene driven by the SV40 promoter. Both constructs were kindly provided by T. Dragic and N. Landau (ADARC, N.Y.). $10^5$ MDM, pretreated with chemokines for 30 min at 37° C., were incubated overnight with HIV-$1_{BaL}$ pseudotypes at a concentration of 50 ng/ml p24. MDM were then washed extensively and medium was replenished but not chemokine-supplemented. After 48 hours, cells were washed, and luciferase activity was measured in lysates according to the manufacturer's instructions (Promega) using a Berthold LB9501 luminometer. All assays were performed in triplicate.

EXAMPLES

Example 1

Selection of RANTES Variants by Biopanning

The interaction between chemokines and their cognate receptors is influenced by cell type-dependent variations in both the quantity and type of cellular components, for example cell surface proteoglycan (31) and intracellular proteins involved in receptor endocytosis (32). The inventors therefore chose to use two different cellular backgrounds, Human Embryonic Kidney (HEK) and Chine Hamster Ovary (CHO), for our biopanning strategy. Three independent biopanning experiments were carried out, each of which features three rounds of selection (and amplification). In two cases, a single cell background was used in each of three rounds (HEK-CCR5; CHO-CCR5), while a third strategy involved alternating the cell background between rounds (HEK-CCR5 & CHO-CCR5). Comparison of the selected sequences enabled us to define a consensus sequence, LSP#SSQSSA (SEQ ID NO: 29).

Table 1 hereunder displays the sequences of clones selected using the "biopanning" strategy from the library of phage-displayed RANTES mutants. Three independent selections, using the indicated target cells, were carried out. Biopanning led to the selection of a consensus sequence (bold), which was different from that obtained via conventional panning on an anti-RANTES antibody. Key to symbols: *=L, M or V; ≠=A, P or S, no T; #=A, P, S or T.

TABLE 1

Sequences of clones selected form the library of phage-displayed RANTES mutants. Three independent selections, using the indicated target cells, were carried out. Cell-based screening led to the definition of a consensus sequence (bold), which was different from that obtained via conventional panning on an anti-RANTES antibody.

| N-terminal sequence of selected clones (SEQ ID NO:) | HEK-CCR5 | CHO-CCR5 | HEK-CCR5 & CHO-CCR5 | Total |
|---|---|---|---|---|
| LSPVSSQSSA (1) (P1) | 6 | | 4 | 10 |
| FSPLSSQSSA (2) (P2) | | 6 | | 6 |
| LSPMSSQSPA (3) | 6 | 1 | 4 | 11 |
| WSPLSSQSPA (4) | 1 | | 1 | 2 |
| WSPLSSQSSP (5) | 2 | | | 2 |
| LSPQSSLSSS (6) | 1 | | | 1 |
| ASSGSSQSTS (7) | 1 | | | 1 |
| ISAGSSELAA (22) | 1 | | | 1 |
| RSPMSSQSSP (9) | 1 | | | 1 |
| YSPSSSLAPA (10) | 1 | | | 1 |
| MSPLSSQASA (11) | | 1 | | 1 |
| ASPLSSQSSS (23) | | 1 | | 1 |
| QSPLSSQAST (13) | | 1 | | 1 |
| QSPLSSTASS (14) | | 1 | | 1 |
| LSPLSSQSAA (15) | | 1 | | 1 |
| GSSSSSQTPA (16) | | | 1 | 1 |
| YSPLSSQSSP (17) | | | 1 | 1 |
| FSSVSSQSSS (18) | | | 1 | 1 |
| Total | 20 | 12 | 12 | 44 |

**LSP*SSQSSA** (25) Consensus (biopanning on CCR5⁺ cells)
RSPPSSR ≠ AS (26) Consensus (panning on 1D2 antibody)
SPYSSDTTP (27) Wild-type RANTES
XS#XSSX### (28) RANTES library
.Key to symbols:
*= L, M or V; ≠ = A, P or S, no T; # = A, P, S or T, X = any amino acid residue.

TABLE 2 hereinafter displays the sequences of clones selected by binding to CHO-CCR5 cells. Selection was based toward Phage clones able to bind cell surface without subsequent internalization.

| N-terminal sequences of selected clones | Number of clones |
|---|---|
| VSTLSSPAST (SEQ ID NO: 30) | 1 |
| ASSFSSRAPP (SEQ ID NO: 31) | 1 |
| QSSASSSSSA (SEQ ID NO: 32) | 1 |
| QSPGSSWSAA (SEQ ID NO: 33) | 1 |
| QSPPSSWSSS (SEQ ID NO: 34) | 2 |
| QSPLSSFTSS (SEQ ID NO: 35) | 1 |
| LSPVSSQSSA (SEQ ID NO: 1) | 1 |
| LSPQSSLSSS (SEQ ID NO: 6) | 5 |
| ASPQSSLPAA (SEQ ID NO: 36) | 4 |

QSPQSSØSSA CONSENSUS 1 (SEQ ID NO: 37)
LSPQSSLSSX CONSENSUS 2 (SEQ ID NO: 38)
XS#XSSX### library* (SEQ ID NO: 28)
Ø = aromatic residue
Key to symbols:
Ø = Aromatic residue, # = A, P, S or T.

At position zero, the residue by which the N-terminus of RANTES is extended, either leucine or one of the aromatic residues was selected. Of the four possible residues at position two (A, P, S or T), we found strong selection for proline, the residue found at this position in the wild-type sequence. At position three, the hydrophobic amino acids leucine, methionine and valine were strongly favoured, but none of the selected clones featured the corresponding wild-type residue, tyrosine. The most striking enrichment was seen at position six (aspartate in wild-type RANTES), where 40 out of 44 clones encoded glutamine. Finally, for positions 7 to 10, where again permutation was restricted to A, P, S or T, we obtained the consensus sequence —SSA—in contrast to the corresponding wild-type sequence, TTP.

In order to ascertain whether the selection of this consensus sequence was indeed CCR5-dependent, we performed three subsequent experiments. Firstly, we used an anti-RANTES antibody that does not interact with the N-terminus of RANTES to screen the library via a conventional panning technique. This would be expected to select for variants that have advantages of stability and/or high expression, whilst conserving the epitope recognized by the antibody. Clones isolated in this way yielded a strikingly different consensus sequence from that obtained via biopanning, notably with arginine and proline ubiquitous in positions 0 and 3, respectively (Table 1). Secondly, biopanning was performed on untransfected HEK or CHO cells. This approach would be expected to favour mutants with enhanced ability to interact with cell surface components other than CCR5, and by default, those merely endowed with a growth advantage. Here, sequence analysis revealed that the RANTES gene had been partially or entirely deleted in the majority of selected phage (data not shown). Finally, we were able to show that the biopanning procedure is capable of selecting phage displayed RANTES mutants capable of inducing CCR5 dependent endocytosis. After incubation at 37° C. with CHO-CCR5 cells, phage encoding the $P_2$ mutant (Table 1) are found in intracellular locations. This effect is not seen with control phage, or when $P_2$-phages are incubated with untransfected CHO cells (FIG. 3).

It is noteworthy that the cell background used did indeed appear to influence the outcome of biopanning. For example, mutant $P_1$ abundant among clones selected on HEK-CCR5 cells, was absent among the panel of clones selected on CHO-CCR5. Conversely, mutant $P_2$ was only present among clones selected on CHO-CCR5 cells (Table 1). With this in mind, the inventors chose to conduct further investigations using the mutant proteins corresponding to both of these clones.

Example 2

Selected RANTES Mutants Show Enhanced Anti-HIV Activity

The RANTES mutants $P_1$ and $P_2$ were prepared by total chemical synthesis. Firstly, we compared their anti-coreceptor activity with that of RANTES in an R5-tropic envelope-mediated cell fusion assay (FIG. 4A). In this assay, both the mutant proteins had extremely potent activities ($IC_{50}$ values of 7 nM (95% confidence limits: 3–15) and 0.6 nM (0.4–0.9)), which compare favourably with that of AOP-RANTES ($IC_{50}$ value of 3 nM (2–6)), while RANTES did not achieve 50% inhibition at the concentrations used. RANTES, unlike AOP-RANTES, achieved only relatively inefficient protection of macrophages from R5-tropic HIV (11). With this in mind, we measured the ability of the RANTES mutants to inhibit entry into MDM in a single-tropic HIV (11). With this in mind, we measured the ability of the RANTES mutants to inhibit entry into MDM in a single-round infectivity assay using HIV-1 particles pseudotyped with the R5 HIV-1 BaL envelope. RANTES was again unable to achieve 50% inhibition at the concentrations used. Both $P_1$ and $P_2$, in contrast, showed enhanced inhibitory potency, especially $P_2$, which was active in the low nanomolar range and exhibited a greater protective effect than AOP-RANTES (FIG. 4B). Finally, we tested the capacity of the selected mutants to inhibit replication of R5-tropic HIV-1 in activated PBMCs. $P_2$ exhibited potency equivalent or superior to that of AOP-RANTES against both the laboratory-adapted HIV-1BaL (data not shown) and the primary isolate, BX08 (FIG. 4C).

Example 3

Mechanism of Action

We sought to investigate the extent to which cell surface receptor blockade and receptor sequestration contribute to the enhanced antiviral activity of the selected RANTES mutants. Firstly, we compared their affinity for CCR5 with that of RANTES, which competes with MIP-1 a with an $IC_{50}$ value of 1.7 nM (95% confidence limits: 0.8–4; see supplementary information). The selected mutants had significantly higher apparent receptor affinity, with $IC_{50}$ values of 0.3 nM (0.2–0.7) and 0.2 nM (0.1–0.3) for $P_1$ and $P_2$, respectively. Subsequently, we measured the ability of the mutants to induce steady-state downmodulation of CCR5 from the surface of CHO-CCR5 cells. Under the experimental conditions used, neither RANTES nor $P_1$ were capable of reducing surface receptor levels below 80% of control levels. In contrast, $P_2$ clearly induced dose-dependent receptor downmodulation with an efficacy comparable to that of AOP-RANTES (FIG. 5). Similar results were obtained using HEK-CCR5 cells (data not shown). We then chose to investigate the ability of the selected RANTES mutants to activate CCR5 using cytosolic calcium flux as a measure of G protein activation (FIG. 6). $P_2$ is a more potent agonist than RANTES at 100 nM on both HEK-CCR5 and CHO-CCR5 cells. Interestingly, the activiy, of $P_1$ appears to be influenced by cellular background; it is similar to that of RANTES on HEK-CCR5 cells but reproducibly and markedly less than that of the wild type on CHO-CCR5 cells. None of the compounds induce calcium flux in untransfected (CCR5—) cells (data not shown).

Finally, the RANTES mutants selected through biopanning on CCR5 appear to be endowed not only with an increased affinity for the receptor, but also with increased selectivity. Indeed, while wild-type RANTES also signals via both CCR1 and CCR3, the mutants P1 and P2 have negligible signaling activity via these two receptors (FIG. 6). It will be interesting to discover whether these ligands have lost their signaling activity because they no longer bind to CCR1 and CCR3, or whether the modifications at their N-termini have produced receptor antagonists. In any case, reduced signaling via CCR1 and CCR3 makes these mutants more attractive as potential anti-HIV agents, since we find, using the same cells, that AOP-RANTES has strong signaling activity via these receptors.

BIBLIOGRAPHY (1) Berger, E. A., Murphy, P. M. & Farber, J. M. (1999) *Annu Rev Immunol* 17: 657–700
(2) Cocchi, F., De Vico, A. L., Garzino, D. A., Arya, S. K., Gallo, R. C. & Lusso, P. (1995) *Science* 270: 1811–5
(3) Bleul, C. C., Farzan, M., Choe, H., Parolin; C., Clark-Lewis, I., Sodroski, J. & Springer, T. A. (1996) *Nature* 382: 829–33
(4) Rollins, B. J. (1997) *Blood* 90: 909–28
(5) Skelton, N. J., Aspiras, F., Ogez, J. & Schall, T. J. (1995) *Biochemistry* 34: 5329–42
(6) Bazan, J. F., Bacon, K. B., Hardiman, G., Wang, W., Soo, K., Rossi, D., Greaves, D. R., Ziotnik, A. & Schall, T. J. (1997) *Nature* 385: 640–4
(7) Imai, T., Baba, M., Nishimura, M., Kakizaki, M., Takagi, S. & Yoshie, 0. (1997) *J. Biol Chem* 272: 15036–42
(8) Wells, T., Proudfoot, A., Power, C. A., Lusti-Narasimhan, M., Alouani, S., Hoogewerf, A. J. & Peitsch, M. C. (1996) *Methods* 10: 126–34
(9) Moser, B., Dewald, B., Barelia, L., Schumacher, C., Baggiolini, M. & Clark-Lewis, I. (1993) *J Biol Chem* 268: 7125–8
(10) Proudfoot, A. E., Power, C. A., Hoogewerf, A. J., Montjovent, M. O., Borlat, F., Offord, R. E. & Wells, T. N. (1996) *J Biol Chem* 271: 2599–603
(11) Simmons, G., Clapham, P. R., Picard, L., Offord, R. E., Rosenkilde, M. M., Schwartz, T. W., Buser, R., Wells, T. N. C. & Proudfoot, A. E. (1997) *Science* 276: 276–9
(12) Mack, M., Luckow, B., Nelson, P. J., Cihak, J., Simmons, G., Clapham, P. R., Signoret, N., Marsh, M., Stangassinger, M., Borlat, F., Wells, T. N., Schlondorff, D. & Proudfoot A. E. (1998) *J Exp Med* 187:1215–24

(13) Signoret, N., Pelchen-Matthews, A., Mack, M., Proudfoot, A. E. & Marsh, M. (2000) *J Cell Biol* 151: 1281–94
(14) Yang, O. O., Swanberg, S. L., Lu, Z., Dziejman, M., McCoy, J., Luster, A. D., Walker, B. D. & Herrmann, S. H. (1999) *J Virol* 73: 4582–9
(15) Townson, J. R., Graham, G. J., Landau, N. R., Rasala, B. & Nibbs, R. J. (2000) *J Biol Chem*
(16) Smith, G. P. (1985) *Science* 228: 1315–7
(17) Clackson T. & Wells, J. A. (1994) *Trends Bioitechnol* 12: 173–84
(18) Brown, K. C. (2000) *Curr Opin Chem Biol* 4: 16–21
(19) Hart, S. L., Knight, A. M., HarbQttle, R. P., Mistry, A., Hunger, H. D., Cutler, D. F., Williamson, R. & Coutelle, C. (1994) *J Biol Chem* 269: 12468–74
(20) Hackeng, T. M., Mounier, C. M., Bon, C., Dawson, P. E., Griffin, J. H. & Kent, S. B. (1997) *Proc Natl Acad Sci USA* 94: 7845–50
(21) Dawson, P. E., Muir, T. W., Clark-Lewis, I. & Kent, S. B. (1994) *Science* 266: 776–9
(22) Wilken, J., Hoover, D., Thompson, D. A., Barlow, P. N., McSparron, H., Picard, L., Wlodawer, A., Lubkowski, J. & Kent, S. B. (1999) *Chem Biol* 6: 43–51
(23) Combadiere, C., Ahuja, S. K., Tiffany, H. L. & Murphy, P. M. (1996) *J Leukoc Biol* 60: 147–52
(24) Combadiere, C., Salzwedel, K., Smith, E. D., Tiffany, H. L., Berger, E. A. & Murphy, P. M. (1998) *J Biol Chem* 273: 23799–804
(25) Pleskoff, O., Treboute, C., Brelot, A., Heveker, N., Seman, M. & Alizon, M. (1997) *Science* 276: 1874–8
(26) Hoogenboom, H. R., Griffiths, A. D., Johnson, K. S., Chiswell, D. J., Hudson, P. & Winter, G. (1991) *Nucleic Acids Res* 19: 4133–7
(27) Nusse, O., Serrander, L., Foyouzi, Y. R., Monod, A., Lew, D. P. & Krause, K. H. (1997) *J Biol Chem* 272, 28360–7
(28) Grynkiewicz, G., Poenie, M. & Tsien, R. Y. (1985) *J Biol Chem* 260: 3440–50
(29) Sabbe, R., Picchio, G. R., Pastore, C., Chaloin, O., Hartley, O., Offord, R. & Mosier, D. E. (2001) *J Virol* 75: 661–71
(30) Connor, R. I., Chen B. K., Choe, S. & Landau, N. R. (1995) *Virology* 206: 935–44
(31) Oravecz, T., Pall, M., Wang, J., Roderiquez, G., Ditto, M. & Norcross, M. A. (1997) *J Immunol* 159: 4587–92
(32) Alkhatib, G., Locati, M., Kennedy, P. E., Murphy, P. M. & Berger, E. A. (1997) *Virology* 234: 340–8
(33) Mosier, D. E., Picchio, G. R., Gulizia, R. J., Sabbe, R., Poignard, P., Picard, L., Offord, R. E., Thompson, D. A. & Wilken, J. (1999) *J. Virol* 73: 3544–3550
(34) Polo, S., Nardese, V., Santis, C. D., Arcelloni, C., Paroni, R., Sironi, F., Verani, A., Rizzi, M., Bolognesi, M. & Lusso, P. (2000) *Eur J Immunol* 30: 3190–8
(35) Vanhoof, G., Goossens, F., De Meester, I., Hendriks, D. & Scharpe, S. (1995) *Faseb J* 9: 736–44
(36) Proost, P., De Meester, I. Schols, D., Struyf, S., Lambeir, A. M., Wuyts, A., Opdenakker, G., De Clercq, E., Scharpe, S. & Van Damme, J. (1998) *J Biol Chem* 273: 7222–7
(37) Pakianathan, D. R., Kuta, E. G., Artis, D. R., Skelton, N. J. & Hebert, C. A. (1997) *Biochemistry* 36: 9642–8
(38). Lowman, H. B. & Wells, J. A. (1993) *J Mol Biol* 234: 564–78
(39) Ferguson, S. S. (2001) *Pharmacol Rev* 53: 1–24
(40) Michael, N. L. & Moore, J. P. (1999) *Nat Med* 5:740–2
(41) Crameri, A., Cwirla, S. & Stemmer, W. P. (1996) *Nat Med* 2: 100–2
(42) Murphy, P. M. (2001) *Nature Immunology* 2: 116–122
(43) Biragyn, A., Tani, K., Grimm, M. C., Weeks, S. & Kwak, L. W. (1999) *Nat Biotechnol* 17: 253–8
(44) Chen, J. D., Bai X., Yang, A. G., Cong, Y. & Chen, S. Y. (1997) *Nat Med* 3: 1110–6
(45) Gerard, C. & Rollins, B. J. (2001) *Nat Immunol* 2: 108–15
(46) Proudfoot, A. E. (2002) *Nat Rev Immunol* 2: 106–15
(47) Balkwill, F. & Mantovani, A. (2001) *Lancet* 357: 53945
(48) Azenshtein, E., Luboshits, G., Shina, S., Neumark, E., Shahbazian, D., Weil, M., Wigler, N., Keydar, I. & Ben Baruch, A (2002) *Cancer Res* 62: 1093–102
(49) Uekusa, Y., Yu, W. G., Mukai, T., Gao, P., Yamaguchi, N., Murai, M., Matsushima, K., Obika, S., Imanishi, T., Higashibata, Y., Nomura, S., Kitamura, Y. Fujiwara, H. & Hamoaka, T. (2002) *Cancer Res* 62: 3751–8.

The invention claimed is:

1. A compound comprising the following formula: Xaa Ser Pro Xaa, Ser Ser Gin Xaa Xaa Xaa—RANTES 10–68 (SEQ ID NO:41) in which
   Xaa at position 1 is L or an aromatic residue,
   Xaa at position 4 is L, M or V
   Xaa at position 8–10 is S, P, T or A.

2. The compound according to claim 1 having one of the following formulae:
   LSPVSSQSSA (SEQ ID NO: 1) RANTES 10–68 (SEQ ID NO. 41).
   FSPLSSQSSA (SEQ ID NO: 2) RANTES 10–68 (SEQ ID NO. 41).
   LSPMSSQSPA (SEQ ID NO:3) RANTES 10–68 (SEQ ID NO. 41)
   WSPLSSQSPA (SEQ ID NO: 4) RANTES 10–68 (SEQ ID NO. 41)
   WSPLSSQSSP (SEQ ID NO: 5) RANTES 10–68 (SEQ ID NO. 41)
   LSPLSSQSAA (SEQ ID NO: 15) RANTES 10–68 (SEQ ID NO. 41)
   YSPLSSQSSP (SEQ ID NO: 17) RANTES 10–68 (SEQ ID NO. 41).

3. A pharmaceutical composition which comprises of a compound having the formula: Xaa Ser Pro Xaa, Ser Ser Gin Xaa Xaa Xaa RANTES 10–68 (SEQ ID NO:41) in which
   Xaa at position 1 is L or an aromatic residue,
   Xaa at position 4 is L, M or V
   Xaa at position 8–10 is 5, P, T or A.
or a pharmaceutical salt thereof, in a mixture with one or more pharmaceutically acceptable excipient.

* * * * *

UNITED STATES PATENT AND TRADEMARK OFFICE
CERTIFICATE OF CORRECTION

PATENT NO. : 7,211,564 B2 Page 1 of 1
APPLICATION NO. : 10/791814
DATED : May 1, 2007
INVENTOR(S) : Guy Gorochov et al.

It is certified that error appears in the above-identified patent and that said Letters Patent is hereby corrected as shown below:

On the title page, please correct the following item (63), under "Related U.S. Application Data" as follows:

(63) Continuation of application No. PCT/EP02/11045, filed on Sept. 5, 2002, which claims priority on U.S. Application No. 09/945,665, filed September 5, 2001.

Signed and Sealed this

Eighteenth Day of March, 2008

JON W. DUDAS
*Director of the United States Patent and Trademark Office*

SEQUENCE LISTING

```
<160> NUMBER OF SEQ ID NOS: 38

<210> SEQ ID NO 1
<211> LENGTH: 10
<212> TYPE: PRT
<213> ORGANISM: Unknown
<220> FEATURE:
<223> OTHER INFORMATION: Cloned peptide sequence selected using the
      biopanning strategy (mammalian)
<400> SEQUENCE: 1

Leu Ser Pro Val Ser Ser Gln Ser Ser Ala
1               5                   10

<210> SEQ ID NO 2
<211> LENGTH: 10
<212> TYPE: PRT
<213> ORGANISM: Unknown
<220> FEATURE:
<223> OTHER INFORMATION: Cloned peptide sequence selected using the
      biopanning strategy (mammalian)
```

-continued

```
<400> SEQUENCE: 2

Phe Ser Pro Leu Ser Ser Gln Ser Ser Ala
1               5                   10

<210> SEQ ID NO 3
<211> LENGTH: 10
<212> TYPE: PRT
<213> ORGANISM: Unknown
<220> FEATURE:
<223> OTHER INFORMATION: Cloned peptide sequence selected using the
      biopanning strategy (mammalian)
<400> SEQUENCE: 3

Leu Ser Pro Met Ser Ser Gln Ser Pro Ala
1               5                   10

<210> SEQ ID NO 4
<211> LENGTH: 10
<212> TYPE: PRT
<213> ORGANISM: Unknown
<220> FEATURE:
<223> OTHER INFORMATION: Cloned peptide sequence selected using the
      biopanning strategy (mammalian)
<400> SEQUENCE: 4

Trp Ser Pro Leu Ser Ser Gln Ser Pro Ala
1               5                   10

<210> SEQ ID NO 5
<211> LENGTH: 10
<212> TYPE: PRT
<213> ORGANISM: Unknown
<220> FEATURE:
<223> OTHER INFORMATION: Cloned peptide sequence selected using the
      biopanning strategy (mammalian)
<400> SEQUENCE: 5

Trp Ser Pro Leu Ser Ser Gln Ser Ser Pro
1               5                   10

<210> SEQ ID NO 6
<211> LENGTH: 10
<212> TYPE: PRT
<213> ORGANISM: Unknown
<220> FEATURE:
<223> OTHER INFORMATION: Cloned peptide sequence selected using the
      biopanning strategy (mammalian)
<400> SEQUENCE: 6

Leu Ser Pro Gln Ser Ser Leu Ser Ser Ser
1               5                   10

<210> SEQ ID NO 7
<211> LENGTH: 10
<212> TYPE: PRT
<213> ORGANISM: Unknown
<220> FEATURE:
<223> OTHER INFORMATION: Cloned peptide sequence selected using the
      biopanning strategy (mammalian)
<400> SEQUENCE: 7

Ala Ser Ser Gly Ser Ser Gln Ser Thr Ser
1               5                   10

<210> SEQ ID NO 8
<211> LENGTH: 10
<212> TYPE: PRT
<213> ORGANISM: Unknown
<220> FEATURE:
<223> OTHER INFORMATION: Cloned peptide sequence selected using the
      biopanning strategy (mammalian)
<400> SEQUENCE: 8
```

```
Ile Ser Ala Gly Ser Ser Gln Ser Thr Ser
1               5                   10

<210> SEQ ID NO 9
<211> LENGTH: 10
<212> TYPE: PRT
<213> ORGANISM: Unknown
<220> FEATURE:
<223> OTHER INFORMATION: Cloned peptide sequence selected using the
      biopanning strategy (mammalian)
<400> SEQUENCE: 9

Arg Ser Pro Met Ser Ser Gln Ser Ser Pro
1               5                   10

<210> SEQ ID NO 10
<211> LENGTH: 10
<212> TYPE: PRT
<213> ORGANISM: Unknown
<220> FEATURE:
<223> OTHER INFORMATION: Cloned peptide sequence selected using the
      biopanning strategy (mammalian)
<400> SEQUENCE: 10

Tyr Ser Pro Ser Ser Ser Leu Ala Pro Ala
1               5                   10

<210> SEQ ID NO 11
<211> LENGTH: 10
<212> TYPE: PRT
<213> ORGANISM: Unknown
<220> FEATURE:
<223> OTHER INFORMATION: Cloned peptide sequence selected using the
      biopanning strategy (mammalian)
<400> SEQUENCE: 11

Met Ser Pro Leu Ser Ser Gln Ala Ser Ala
1               5                   10

<210> SEQ ID NO 12
<211> LENGTH: 10
<212> TYPE: PRT
<213> ORGANISM: Unknown
<220> FEATURE:
<223> OTHER INFORMATION: Cloned peptide sequence selected using the
      biopanning strategy (mammalian)
<400> SEQUENCE: 12

Ala Ser Pro Met Ser Ser Gln Ser Ser Ser
1               5                   10

<210> SEQ ID NO 13
<211> LENGTH: 10
<212> TYPE: PRT
<213> ORGANISM: Unknown
<220> FEATURE:
<223> OTHER INFORMATION: Cloned peptide sequence selected using the
      biopanning strategy (mammalian)
<400> SEQUENCE: 13

Gln Ser Pro Leu Ser Ser Gln Ala Ser Thr
1               5                   10

<210> SEQ ID NO 14
<211> LENGTH: 10
<212> TYPE: PRT
<213> ORGANISM: Unknown
<220> FEATURE:
<223> OTHER INFORMATION: Cloned peptide sequence selected using the
      biopanning strategy (mammalian)
<400> SEQUENCE: 14
```

Gln Ser Pro Leu Ser Ser Thr Ala Ser Ser
1               5                   10

<210> SEQ ID NO 15
<211> LENGTH: 10
<212> TYPE: PRT
<213> ORGANISM: Unknown
<220> FEATURE:
<223> OTHER INFORMATION: Cloned peptide sequence selected using the
      biopanning strategy (mammalian)
<400> SEQUENCE: 15

Leu Ser Pro Leu Ser Ser Gln Ser Ala Ala
1               5                   10

<210> SEQ ID NO 16
<211> LENGTH: 10
<212> TYPE: PRT
<213> ORGANISM: Unknown
<220> FEATURE:
<223> OTHER INFORMATION: Cloned peptide sequence selected using the
      biopanning strategy (mammalian)
<400> SEQUENCE: 16

Gly Ser Ser Ser Ser Ser Gln Thr Pro Ala
1               5                   10

<210> SEQ ID NO 17
<211> LENGTH: 10
<212> TYPE: PRT
<213> ORGANISM: Unknown
<220> FEATURE:
<223> OTHER INFORMATION: Cloned peptide sequence selected using the
      biopanning strategy (mammalian)
<400> SEQUENCE: 17

Tyr Ser Pro Leu Ser Ser Gln Ser Ser Pro
1               5                   10

<210> SEQ ID NO 18
<211> LENGTH: 10
<212> TYPE: PRT
<213> ORGANISM: Unknown
<220> FEATURE:
<223> OTHER INFORMATION: Cloned peptide sequence selected using the
      biopanning strategy (mammalian)
<400> SEQUENCE: 18

Phe Ser Ser Val Ser Ser Gln Ser Ser Ser
1               5                   10

<210> SEQ ID NO 19
<211> LENGTH: 9
<212> TYPE: PRT
<213> ORGANISM: Artificial sequence
<220> FEATURE:
<223> OTHER INFORMATION: tag HA 1.1 peptide sequence

<400> SEQUENCE: 19

Tyr Pro Tyr Asp Val Pro Asp Tyr Ala
1               5

<210> SEQ ID NO 20
<211> LENGTH: 39
<212> TYPE: DNA
<213> ORGANISM: Artificial sequence
<220> FEATURE:
<223> OTHER INFORMATION: PCR downstream primer

<400> SEQUENCE: 20
tggggcccct ctagacatct ccaaagagtt gatgtactc                          39

<210> SEQ ID NO 21
<211> LENGTH: 99
<212> TYPE: DNA
<213> ORGANISM: Artificial sequence
<220> FEATURE:
<223> OTHER INFORMATION: PCR upstream primer
<220> FEATURE:
<221> NAME/KEY: Unsure
<222> LOCATION: (25)..(25)
<223> OTHER INFORMATION: n = a, t, c or g
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (31)..(31)
<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (46)..(46)
<223> OTHER INFORMATION: n is a, c, g, or t
<220> FEATURE:
<221> NAME/KEY: misc_feature
<222> LOCATION: (49)..(49)
<223> OTHER INFORMATION: n is a, c, g, or t
<220> FEATURE:
<221> NAME/KEY: misc_feature
<222> LOCATION: (52)..(52)
<223> OTHER INFORMATION: n is a, c, g, or t

<400> SEQUENCE: 21
ctcgcggccc agccggccat ggccnnktcc ncannktcct cgnnknccnc ancctgctgc    60
tttgcctaca ttgcgcggcc gctgccccgt gcccacatc                          99

<210> SEQ ID NO 22
<211> LENGTH: 10
<212> TYPE: PRT
<213> ORGANISM: Unknown
<220> FEATURE:
<223> OTHER INFORMATION: Cloned peptide sequence selected using the
      biopanning strategy (mammalian)
<400> SEQUENCE: 22

Ile Ser Ala Gly Ser Ser Glu Leu Ala Ala
1               5                   10

<210> SEQ ID NO 23
<211> LENGTH: 10
<212> TYPE: PRT
<213> ORGANISM: Unknown
<220> FEATURE:
<223> OTHER INFORMATION: Cloned peptide sequence selected using the
      biopanning strategy (mammalian)
<400> SEQUENCE: 23

Ala Ser Pro Leu Ser Ser Gln Ser Ser Ser
1               5                   10

<210> SEQ ID NO 24
<211> LENGTH: 10
<212> TYPE: PRT
<213> ORGANISM: Artificial Sequence
<220> FEATURE:

```
<223> OTHER INFORMATION: Synthetic peptide (page 9 of specification)
<220> FEATURE:
<221> NAME/KEY: UNSURE
<222> LOCATION: (1)..(1)
<223> OTHER INFORMATION: Xaa = L or an aromatic residue
<220> FEATURE:
<221> NAME/KEY: UNSURE
<222> LOCATION: (3)..(3)
<223> OTHER INFORMATION: Xaa = S,P,T or A
<220> FEATURE:
<221> NAME/KEY: UNSURE
<222> LOCATION: (4)..(4)
<223> OTHER INFORMATION: Xaa = L, M or V
<220> FEATURE:
<221> NAME/KEY: UNSURE
<222> LOCATION: (8)..(10)
<223> OTHER INFORMATION: Xaa = S,P,T or A

<400> SEQUENCE: 24

Xaa Ser Xaa Xaa Ser Ser Gln Xaa Xaa Xaa
1               5                   10

<210> SEQ ID NO 25
<211> LENGTH: 10
<212> TYPE: PRT
<213> ORGANISM: Artificial Sequence
<220> FEATURE:
<223> OTHER INFORMATION: Consensus biopanning on CCR5 cells
<220> FEATURE:
<221> NAME/KEY: UNSURE
<222> LOCATION: (4)..(4)
<223> OTHER INFORMATION: Xaa = L, M or V

<400> SEQUENCE: 25

Leu Ser Pro Xaa Ser Ser Gln Ser Ser Ala
1               5                   10

<210> SEQ ID NO 26
<211> LENGTH: 10
<212> TYPE: PRT
<213> ORGANISM: Artificial Sequence
<220> FEATURE:
<223> OTHER INFORMATION: Consensus biopanning on 1D2 antibody
<220> FEATURE:
<221> NAME/KEY: UNSURE
<222> LOCATION: (8)..(8)
<223> OTHER INFORMATION: Xaa = A, P or S

<400> SEQUENCE: 26

Arg Ser Pro Pro Ser Ser Arg Xaa Ala Ser
1               5                   10

<210> SEQ ID NO 27
<211> LENGTH: 9
<212> TYPE: PRT
<213> ORGANISM: Artificial Sequence
<220> FEATURE:
<223> OTHER INFORMATION: Wild-type RANTES

<400> SEQUENCE: 27

Ser Pro Tyr Ser Ser Asp Thr Thr Pro
1               5

<210> SEQ ID NO 28
<211> LENGTH: 10
<212> TYPE: PRT
<213> ORGANISM: Artificial Sequence
<220> FEATURE:
<223> OTHER INFORMATION: RANTES library
<220> FEATURE:
<221> NAME/KEY: UNSURE
```

```
<222> LOCATION: (1)..(1)
<223> OTHER INFORMATION: Xaa = any amino acid, unknown or other
<220> FEATURE:
<221> NAME/KEY: UNSURE
<222> LOCATION: (3)..(3)
<223> OTHER INFORMATION: Xaa = A, P, S or T
<220> FEATURE:
<221> NAME/KEY: UNSURE
<222> LOCATION: (4)..(4)
<223> OTHER INFORMATION: Xaa = any amino acid, unknown or other
<220> FEATURE:
<221> NAME/KEY: UNSURE
<222> LOCATION: (7)..(7)
<223> OTHER INFORMATION: Xaa = any amino acid, unknown or other
<220> FEATURE:
<221> NAME/KEY: UNSURE
<222> LOCATION: (8)..(10)
<223> OTHER INFORMATION: Xaa = A, P, S or T

<400> SEQUENCE: 28

Xaa Ser Xaa Xaa Ser Ser Xaa Xaa Xaa Xaa
1               5                   10

<210> SEQ ID NO 29
<211> LENGTH: 10
<212> TYPE: PRT
<213> ORGANISM: Artificial Sequence
<220> FEATURE:
<223> OTHER INFORMATION: Consensus biopanning sequence
<220> FEATURE:
<221> NAME/KEY: UNSURE
<222> LOCATION: (4)..(4)
<223> OTHER INFORMATION: Xaa = A, P, S or T

<400> SEQUENCE: 29

Leu Ser Pro Xaa Ser Ser Gln Ser Ser Ala
1               5                   10

<210> SEQ ID NO 30
<211> LENGTH: 10
<212> TYPE: PRT
<213> ORGANISM: Unknown
<220> FEATURE:
<223> OTHER INFORMATION: Cloned peptide sequence (mammalian)

<400> SEQUENCE: 30

Val Ser Thr Leu Ser Ser Pro Ala Ser Thr
1               5                   10

<210> SEQ ID NO 31
<211> LENGTH: 10
<212> TYPE: PRT
<213> ORGANISM: Unknown
<220> FEATURE:
<223> OTHER INFORMATION: Cloned peptide sequence (mammalian)

<400> SEQUENCE: 31

Ala Ser Ser Phe Ser Ser Arg Ala Pro Pro
1               5                   10

<210> SEQ ID NO 32
<211> LENGTH: 10
<212> TYPE: PRT
<213> ORGANISM: Unknown
<220> FEATURE:
<223> OTHER INFORMATION: Cloned peptide sequence (mammalian)

<400> SEQUENCE: 32

Gln Ser Ser Ala Ser Ser Ser Ser Ser Ala
1               5                   10
```

```
<210> SEQ ID NO 33
<211> LENGTH: 10
<212> TYPE: PRT
<213> ORGANISM: Unknown
<220> FEATURE:
<223> OTHER INFORMATION: Cloned peptide sequence (mammalian)

<400> SEQUENCE: 33

Gln Ser Pro Gly Ser Ser Trp Ser Ala Ala
1               5                   10

<210> SEQ ID NO 34
<211> LENGTH: 10
<212> TYPE: PRT
<213> ORGANISM: Unknown
<220> FEATURE:
<223> OTHER INFORMATION: Cloned peptide sequence (mammalian)

<400> SEQUENCE: 34

Gln Ser Pro Pro Ser Ser Trp Ser Ser Ser
1               5                   10

<210> SEQ ID NO 35
<211> LENGTH: 10
<212> TYPE: PRT
<213> ORGANISM: Unknown
<220> FEATURE:
<223> OTHER INFORMATION: Cloned peptide sequence (mammalian)

<400> SEQUENCE: 35

Gln Ser Pro Leu Ser Ser Phe Thr Ser Ser
1               5                   10

<210> SEQ ID NO 36
<211> LENGTH: 10
<212> TYPE: PRT
<213> ORGANISM: Unknown
<220> FEATURE:
<223> OTHER INFORMATION: Cloned peptide sequence (mammalian)

<400> SEQUENCE: 36

Ala Ser Pro Gln Ser Ser Leu Pro Ala Ala
1               5                   10

<210> SEQ ID NO 37
<211> LENGTH: 10
<212> TYPE: PRT
<213> ORGANISM: Artificial Sequence
<220> FEATURE:
<223> OTHER INFORMATION: Consensus sequence 1
<220> FEATURE:
<221> NAME/KEY: Unsure
<222> LOCATION: (7)..(7)
<223> OTHER INFORMATION: Aromatic Residue

<400> SEQUENCE: 37

Gln Ser Pro Gln Ser Ser Xaa Ser Ser Ala
1               5                   10

<210> SEQ ID NO 38
<211> LENGTH: 10
<212> TYPE: PRT
<213> ORGANISM: Artificial Sequence
<220> FEATURE:
<223> OTHER INFORMATION: Consensus sequence 2
<220> FEATURE:
<221> NAME/KEY: misc_feature
```

```
<222> LOCATION: (10)..(10)
<223> OTHER INFORMATION: Xaa can be any naturally occurring amino acid

<400> SEQUENCE: 38

Leu Ser Pro Gln Ser Ser Leu Ser Ser Xaa
1               5                   10
```